US010040876B2

(12) United States Patent
Oh et al.

(10) Patent No.: US 10,040,876 B2
(45) Date of Patent: Aug. 7, 2018

(54) CONJUGATED DIENE-BASED POLYMER

(71) Applicant: LG Chem, Ltd., Seoul (KR)

(72) Inventors: Kyoung Hwan Oh, Daejeon (KR);
Won Hee Kim, Daejeon (KR); Hyo Jin Bae, Daejeon (KR); Jeong Heon Ahn, Daejeon (KR); Woo Jin Cho, Daejeon (KR); Suk Youn Kang, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/503,900

(22) PCT Filed: Nov. 18, 2015

(86) PCT No.: PCT/KR2015/012425
§ 371 (c)(1),
(2) Date: Feb. 14, 2017

(87) PCT Pub. No.: WO2016/080765
PCT Pub. Date: May 26, 2016

(65) Prior Publication Data
US 2017/0275401 A1    Sep. 28, 2017

(30) Foreign Application Priority Data

Nov. 20, 2014 (KR) .................. 10-2014-0162931
Nov. 20, 2014 (KR) .................. 10-2014-0162935
Nov. 17, 2015 (KR) .................. 10-2015-0161320

(51) Int. Cl.
| C08F 36/06 | (2006.01) |
| C08K 5/09 | (2006.01) |
| C08F 4/54 | (2006.01) |
| C07F 5/06 | (2006.01) |
| C08F 36/04 | (2006.01) |
| C08F 2/06 | (2006.01) |
| C08F 2/38 | (2006.01) |
| C08F 4/60 | (2006.01) |
| C08F 4/622 | (2006.01) |
| C08L 9/00 | (2006.01) |
| B60C 1/00 | (2006.01) |
| C08F 4/06 | (2006.01) |
| C08F 4/619 | (2006.01) |

(52) U.S. Cl.
CPC .............. *C08F 36/06* (2013.01); *B60C 1/00* (2013.01); *C07F 5/068* (2013.01); *C08F 2/06* (2013.01); *C08F 2/38* (2013.01); *C08F 4/06* (2013.01); *C08F 4/545* (2013.01); *C08F 4/619* (2013.01); *C08F 4/622* (2013.01); *C08F 36/04* (2013.01); *C08K 5/09* (2013.01); *C08L 9/00* (2013.01); *Y02T 10/862* (2013.01)

(58) Field of Classification Search
CPC .. C08F 2/06; C08F 4/545; C08F 36/04; C08F 36/06; C07F 5/068
USPC ................................ 526/164, 340.4
See application file for complete search history.

(56) References Cited

U.S. PATENT DOCUMENTS

| 5,905,125 | A | * | 5/1999 | Tsujimoto | ............. C08F 136/06 526/138 |
| 6,391,990 | B1 | * | 5/2002 | Ishino | ..................... C08F 36/04 526/143 |
| 7,288,611 | B2 | * | 10/2007 | Jiang | ..................... C08F 36/06 502/107 |
| 2006/0089472 | A1 | | 4/2006 | Viola et al. | |
| 2007/0149717 | A1 | | 6/2007 | Luo et al. | |
| 2008/0182954 | A1 | | 7/2008 | Luo et al. | |
| 2009/0253892 | A1 | | 10/2009 | Bischoff et al. | |
| 2012/0100934 | A1 | | 4/2012 | Sullivan et al. | |
| 2015/0299350 | A1 | | 10/2015 | Qin et al. | |

FOREIGN PATENT DOCUMENTS

| EP | 1055659 A1 | 11/2000 |
| EP | 1840162 A1 | 10/2007 |
| EP | 3106473 A1 | 12/2016 |
| JP | 2004211048 A | 7/2004 |
| KR | 19990071124 A | 9/1999 |
| KR | 20060049136 A | 5/2006 |
| KR | 20080063191 A | 7/2008 |
| KR | 101363693 B1 | 2/2014 |
| KR | 20140129048 A | 11/2014 |

OTHER PUBLICATIONS

Online translation of Detailed Description of JP 2004-211048A; publication date: Jul. 29, 2004.*
International Search Report from PCT/KR2015/012425, dated Feb. 26, 2016.
Supplementary European Search Report for Application No. EP15860487, dated Oct. 19, 2017.

* cited by examiner

*Primary Examiner* — Fred M Teskin
(74) *Attorney, Agent, or Firm* — Lerner, David, Littenberg, Krumholz & Mentlik, LLP

(57) ABSTRACT

The present invention provides 1,4-cis polybutadiene having high linearity with an −S/R value of 1 or greater at 100° C., and accordingly, is capable of reducing resistance properties, particularly rolling resistance, and greatly enhancing fuel efficiency properties when used in a rubber composition.

19 Claims, No Drawings

CONJUGATED DIENE-BASED POLYMER

CROSS-REFERENCE TO RELATED APPLICATION

This application is a national phase entry under 35 U.S.C. § 371 of International Application No. PCT/KR2015/012425, filed Nov. 18, 2015, which claims priority to Korean Application No. 10-2014-0162931, filed Nov. 20, 2014, Korean Application No. 10-2014-0162935, filed Nov. 20, 2014, and Korean Application No. 10-2015-0161320, filed Nov. 17, 2015, the disclosures of which are incorporated herein by reference.

FIELD OF THE INVENTION

The present invention relates to a conjugated diene-based polymer, and in particular, to cis 1,4-cis polybutadiene having a –S/R (stress/relaxation) value of 1 or greater at 100° C.

DESCRIPTION OF THE RELATED ART

With increasing demands for rubber compositions in various manufacturing fields such as tires, shoe soles or golf balls, values of conjugated diene-based polymers, particularly butadiene-based polymers among these, which are synthetic rubber, have increased as a substitute for natural rubber that faces product shortfall.

Generally, linearity or branching of conjugated diene-based polymers greatly affects physical properties of polymers. Specifically, melting rates and viscosity properties of polymers increase as linearity decreases and branching increases, and as a result, polymer processibility is enhanced. However, when branching of polymers is high, molecular weight distribution becomes wide, and mechanical properties of the polymers affecting abrasion resistance, crack resistance, a rebound property or the like of a rubber composition decline.

In addition, linearity or branching of conjugated diene-based polymers, particularly butadiene-based polymers, is greatly influenced by the content of cis-1,4 bonds included in the polymer. Linearity increases as cis-1,4 bond content in a conjugated diene-based polymer increases, and as a result, the polymer has excellent mechanical properties and may enhance abrasion resistance, crack resistance and a rebound property of a rubber composition.

Accordingly, various methods for preparing a conjugated diene-based polymer having suitable processibility while increasing linearity by increasing cis-1,4 bond content in the conjugated diene-based polymer have been researched and developed.

Specifically, a method using a polymerization system including a lanthanide rare earth element-containing compound, particularly a neodymium-based compound, has been proposed. However, conjugated diene-based polymers prepared through the method using the polymerization system do not have high cis-1,4 bond content, and therefore, physical property improving effects of a rubber composition were not sufficient.

In addition, a method for preparing a conjugated diene-based polymer by preforming a catalyst composition including an organic aluminum compound, a halogen compound and butadiene together with a neodymium-based compound, and carrying out a polymerization reaction of a conjugated diene-based monomer using the same has been proposed. However, the method normally uses diisobutylaluminum hydride (DIBAH) as an aluminum-based compound capable of performing molecular weight modification as well as alkylation, and DIBAH included in a catalyst composition causes various problems during processes when preparing a conjugated diene-based polymer. In detail, in the above-mentioned method, preforming is carried out adding a small amount of butadiene in order to reduce the production of various active catalyst species in the alkylation step using DIBAH, and herein, a problem of processibility decline occurs by polymers produced through the preforming of butadiene blocking a catalyst input line of a polymerization reactor. In addition, there is a problem in that molecular weights are not readily modified in the method, and it takes long until changes in the molecular weight modification are identified. Particularly, conjugated diene-based polymers having many short chain branches and low linearity, that is, having an –S/R (stress/relaxation) value of less than 1 at 100° C. are prepared since chain transfer often occurs during the polymerization reaction in the above-mentioned method. However, conjugated diene-based polymers having an –S/R value of less than 1 as above have a problem in that resistance properties, particularly rolling resistance (RR), of a rubber composition increase due to a high degree of branching, and fuel efficiency properties decline as a result.

In view of the above, development of methods capable of preparing conjugated diene-based polymers having high linearity through uniformization of active catalyst species, and quick and simple molecular weight modification has been required.

DISCLOSURE OF THE INVENTION

Technical Problem

An object of the present invention is to provide 1,4-cis polybutadiene having high linearity and thereby reducing resistance properties, particularly rolling resistance, when used in a rubber composition, and as a result, capable of enhancing fuel efficiency properties.

Another object of the present invention is to provide a rubber composition exhibiting excellent resistance properties and fuel efficiency properties by including the 1,4-cis polybutadiene, and a tire component manufactured using the 1,4-cis polybutadiene.

Technical Solution

In view of the above, the present invention has the following constitutions:

(1) 1,4-Cis polybutadiene having a –S/R (stress/relaxation) value of 1 or greater at 100° C.

(2) The 1,4-cis polybutadiene described in (1) having a ratio (Mw/Mn) of a weight average molecular weight (Mw) to a number average molecular weight (Mn) of 3 or less.

(3) The 1,4-cis polybutadiene described in (1) or (2) having a weight average molecular weight (Mw) of 400,000 g/mol to 2,500,000 g/mol and a number average molecular weight (Mn) of 100,000 g/mol to 1,000,000 g/mol.

(4) The 1,4-cis polybutadiene described in any one of (1) to (3) having Mooney viscosity of 30 to 90 at 100° C.

(5) The 1,4-cis polybutadiene described in any one of (1) to (4) having 95% or higher cis-1,4 bond content.

(6) The 1,4-cis polybutadiene described in any one of (1) to (5) obtained through polymerization reacting a mixture of a molecular weight modifier and, as a monomer, 1,3-butadiene or a butadiene derivative using a catalyst composition, wherein the catalyst composition includes a lanthanide rare earth element-containing compound, modified methylaluminoxane, a halogen compound and an aliphatic hydrocarbon-based solvent.

(7) The 1,4-cis polybutadiene described in (6), wherein the molecular weight modifier includes any one or a mixture of two or more selected from the group consisting of trihydrocarbylaluminum, dihydrocarbylaluminum hydride, hydrogen and silane compounds.

(8) The 1,4-cis polybutadiene described in (6) or (7), wherein the molecular weight modifier is used in a molar ratio of 1 to 100 with respect to 1 mol of the lanthanide rare earth element-containing compound.

(9) The 1,4-cis polybutadiene described in any one of (6) to (8), wherein the catalyst composition is a pre-mixture of the lanthanide rare earth element-containing compound, the modified methylaluminoxane, the halogen compound and the aliphatic hydrocarbon-based solvent.

(10) The 1,4-cis polybutadiene described in any one of (6) to (9), wherein the catalyst composition includes the lanthanide rare earth element-containing compound in an amount of 0.01 mmol to 0.25 mmol with respect to 100 g of the monomer.

(11) The 1,4-cis polybutadiene described in any one of (6) to (10), wherein the catalyst composition includes the lanthanide rare earth element-containing compound in 0.01 mmol to 0.25 mmol, the modified methylaluminoxane in 0.05 mmol to 50.0 mmol, the halogen compound in 0.01 mmol to 2.5 mmol and the aliphatic hydrocarbon-based solvent in 5 mmol to 200 mmol with respect to 100 g of the monomer.

(12) The 1,4-cis polybutadiene described in any one of (6) to (11), wherein the catalyst composition includes the lanthanide rare earth element-containing compound and the modified methylaluminoxane in a molar ratio of 1.0:5.0 to 1.0:200.

(13) The 1,4-cis polybutadiene described in any one of (6) to (12), wherein the catalyst composition includes the modified methylaluminoxane in 5 mols to 200 mols, the halogen compound in 1 mol to 10 mols and the aliphatic hydrocarbon-based solvent in 20 mols to 20,000 mols with respect to 1 mol of the lanthanide rare earth element-containing compound.

(14) The 1,4-cis polybutadiene described in any one of (6) to (13), wherein the lanthanide rare earth element-containing compound includes a neodymium compound of the following Chemical Formula 1:

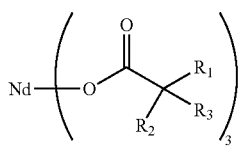

[Chemical Formula 1]

wherein, in Chemical Formula 1, $R_1$ to $R_3$ are each independently a hydrogen atom, or a linear or branched alkyl group having 1 to 12 carbon atoms.

(15) The 1,4-cis polybutadiene described in any one of (6) to (14), wherein the lanthanide rare earth element-containing compound includes a neodymium compound in which, in Chemical Formula 1, $R_1$ is a linear or branched alkyl group having 6 to 12 carbon atoms, and $R_2$ and $R_3$ are each independently a hydrogen atom or a linear or branched alkyl group having 2 to 8 carbon atoms, but $R_2$ and $R_3$ are not both hydrogen atoms at the same time.

(16) The 1,4-cis polybutadiene described in any one of (6) to (15), wherein the lanthanide rare earth element-containing compound includes any one or a mixture of two or more selected from the group consisting of Nd(2,2-diethyl decanoate)$_3$, Nd(2,2-dipropyl decanoate)$_3$, Nd(2,2-dibutyl decanoate)$_3$, Nd(2,2-dihexyl decanoate)$_3$, Nd(2,2-dioctyl decanoate)$_3$, Nd(2-ethyl-2-propyl decanoate)$_3$, Nd(2-ethyl-2-butyl decanoate)$_3$, Nd(2-ethyl-2-hexyl decanoate)$_3$, Nd(2-propyl-2-butyl decanoate)$_3$, Nd(2-propyl-2-hexyl decanoate)$_3$, Nd(2-propyl-2-isopropyl decanoate)$_3$, Nd(2-butyl-2-hexyl decanoate)$_3$, Nd(2-hexyl-2-octyl decanoate)$_3$, Nd(2-t-butyl decanoate)$_3$, Nd(2,2-diethyl octanoate)$_3$, Nd(2,2-dipropyl octanoate)$_3$, Nd(2,2-dibutyl octanoate)$_3$, Nd(2,2-dihexyl octanoate)$_3$, Nd(2-ethyl-2-propyl octanoate)$_3$, Nd(2-ethyl-2-hexyl octanoate)$_3$, Nd(2,2-diethyl nonanoate)$_3$, Nd(2,2-dipropyl nonanoate)$_3$, Nd(2,2-dibutyl nonanoate)$_3$, Nd(2,2-dihexyl nonanoate)$_3$, Nd(2-ethyl-2-propyl nonanoate)$_3$ and Nd(2-ethyl-2-hexyl nonanoate)$_3$.

(17) The 1,4-cis polybutadiene described in any one of (6) to (16), wherein, in the modified methylaluminoxane, mol % to 90 mol % of a methyl group of the methylaluminoxane is substituted with a hydrocarbon group having 2 to 20 carbon atoms.

(18) The 1,4-cis polybutadiene described in (17), wherein the hydrocarbon group is a linear or branched alkyl group having 2 to 10 carbon atoms.

(19) The 1,4-cis polybutadiene described in any one of (6) to (18), wherein the aliphatic hydrocarbon-based solvent includes any one or a mixture of two or more selected from the group consisting of linear, branched or cyclic aliphatic hydrocarbon having 5 to 20 carbon atoms.

(20) The 1,4-cis polybutadiene described in any one of (6) to (19), wherein the halogen compound includes any one or a mixture of two or more selected from the group consisting of elemental halogen compounds, interhalogen compounds, halogenated hydrogen, organic halides, non-metal halides, metal halides and organic metal halides.

(21) The 1,4-cis polybutadiene described in any one of (6) to (20), wherein the catalyst composition does not include diisobutylaluminum hydride.

(22) A rubber composition including the 1,4-cis polybutadiene described in any one of (1) to (21).

(23) A tire component manufactured using the 1,4-cis polybutadiene described in any one of (1) to (21).

Advantageous Effects 1,4-Cis polybutadiene according to the present invention has high linearity with an –S/R value of 1 or greater at 100° C., and accordingly, is capable of reducing resistance properties, particularly rolling resistance, and greatly enhancing fuel efficiency properties when used in a rubber composition.

MODE FOR CARRYING OUT THE INVENTION

Hereinafter, the present invention will be described in more detail in order to illuminate the present invention. Terms or words used in the present specification and the claims are not to be interpreted limitedly to common or dictionary definitions, and shall be interpreted as meanings and concepts corresponding to technological ideas of the present invention based on a principle in which the inventors may suitably define the concepts of terms in order to describe the invention in the best possible way.

A term "preforming" used in the present specification means pre-polymerization in a catalyst composition for conjugated diene-based polymer or 1,4-cis polybutadiene preparation. Specifically, when a catalyst composition including a lanthanide rare earth element-containing compound, an aluminum compound and a halogen compound includes diisobutylaluminum hydride (DIBAH) as the aluminum compound, the catalyst composition also includes a small amount of monomers such as butadiene in order to reduce the possibility of various active catalyst species production. Accordingly, pre-polymerization of butadiene is carried out in the catalyst composition for 1,4-cis polybutadiene preparation prior to a polymerization reaction for preparing 1,4-cis polybutadiene, and this is referred to as preforming.

In addition, a term "premixing" used in the present specification means a state in which each constituent is uniformly mixed in a catalyst composition without being polymerized.

In the present invention, 1,4-cis polybutadiene having a high –S/R value of 1 or greater at 100° C. is prepared through optimizing a catalyst composition for forming a conjugated diene polymer and a preparation method using the catalyst composition, and as a result, resistance properties and fuel efficiency properties are capable of being enhanced when used in a rubber composition.

The –S/R value represents changes in stress shown as a reaction for the same amount of strain generated in a material, and is an index representing polymer linearity. A lower –S/R value commonly means lower 1,4-cis polybutadiene linearity, and as linearity decreases, rolling resistance increases when used in a rubber composition. In addition, a degree of branching and molecular weight distribution may be predicted from the –S/R value. As the –S/R value decreases, the degree of branching increases, and the molecular weight distribution becomes wider, and as a result, mechanical properties are poor whereas polymer processibility is superior.

1,4-cis polybutadiene according to one embodiment of the present invention is a polymer having high linearity with a –S/R (stress/relaxation) value of 1 or greater at 100° C. More specifically, a –S/R value of the 1,4-cis polybutadiene is from 1 to 1.2, and even more specifically from 1.045 to 1.2.

In the present invention, the –S/R value may be measured using a Mooney viscometer, for example, a Large Rotor of MV2000E manufactured by Monsanto under a condition of 100° C. and Rotor Speed 2±0.02 rpm. Specifically, the polymer is left unattended for 30 minutes or longer at room temperature (23±5° C.), 27±3 g thereof is collected and inside a die cavity is filled with the polymer sample, and Mooney viscosity is measured while operating a Platen and applying Torque, and by measuring a slope of Mooney viscosity changes appearing while releasing Torque, the –S/R value may be determined.

In addition, the 1,4-cis polybutadiene according to one embodiment of the present invention may have narrow molecular weight distribution having polydispersity (PDI) of 3 or less. When the 1,4-cis polybutadiene has PDI of greater than 3, there is concern that mechanical properties such as abrasion resistance and impact resistance decline when used in a rubber composition. When considering the significance of mechanical property improving effects of the polymer due to PDI control, PDI of the conjugated diene-based polymer may be specifically from 2.0 to 2.5, and more specifically from 2.35 to 2.5.

In the present invention, PDI of 1,4-cis polybutadiene is also referred to as molecular weight distribution (MWD), and may be calculated from a ratio (Mw/Mn) of a weight average molecular weight (Mw) to a number average molecular weight (Mn). Herein, the number average molecular weight (Mn) is a common average of individual molecular weights of polymers calculated by measuring molecular weights of n polymer molecules, and dividing the sum of these molecular weights by n, and the weight average molecular weight (Mw) represents molecular weight distribution of a polymer composition, and may be calculated by the following Mathematical Formula 1.

$$M_w = \frac{\sum_i N_i M_i^2}{\sum_i N_i M_i}$$ [Mathematical Formula 1]

In Mathematical Formula 1, Ni is the number of molecules having a molecular weight of Mi. An average of all molecular weights may be represented by gram per mol (g/mol).

Furthermore, in the present invention, the weight average molecular weight and the number average molecular weight are each a polystyrene converted molecular weight analyzed with gel permeation chromatography (GPC).

In addition, the 1,4-cis polybutadiene according to one embodiment of the present invention may have a weight average molecular weight (Mw) of 400,000 g/mol to 2,500,000 g/mol and specifically 1,100,000 g/mol to 2,300,000 g/mol while satisfying the polydispersity condition. Furthermore, the 1,4-cis polybutadiene according to one embodiment of the present invention may have a number average molecular weight (Mn) of 100,000 g/mol to 1,000,000 g/mol and specifically 500,000 g/mol to 900,000 g/mol. When the weight average molecular weight (Mw) of the 1,4-cis polybutadiene is less than 400,000 g/mol or the number average molecular weight (Mn) is less than 100,000 g/mol, there is concern of an increase in hysteresis loss due to elasticity decline of a vulcanizate, and degeneration of abrasion resistance. In addition, when the weight average molecular weight (Mw) is greater than 2,500,000 g/mol or the number average molecular weight (Mn) is greater than 1,000,000 g/mol, processibility of the 1,4-cis polybutadiene declines causing degeneration in the workability of a rubber composition, and mixing and kneading become difficult, and as a result, physical properties of the rubber composition may be difficult to be sufficiently enhanced.

More specifically, when the 1,4-cis polybutadiene according to one embodiment of the present invention satisfies weight average molecular weight (Mw) and number average molecular weight conditions while also satisfying the –S/R and the PDI, mechanical properties, elasticity and processibility may be improved in a balanced way without inclining to any one of these when the 1,4-cis polybutadiene is used in a rubber composition.

Specifically the 1,4-cis polybutadiene may have PDI of 3 or less, a weight average molecular weight (Mw) of 400,000 g/mol to 2,500,000 g/mol and a number average molecular weight (Mn) of 100,000 g/mol to 1,000,000 g/mol while also satisfying the –S/R condition. More specifically, the 1,4-cis polybutadiene may have PDI of 2 to 2.5, a weight average molecular weight (Mw) of 700,000 g/mol to 2,300,000 g/mol and a number average molecular weight (Mn) of 300,000 g/mol to 900,000 g/mol, and even more specifically may have PDI of 2.35 to 2.5, a weight average molecular weight (Mw) of 1,100,000 g/mol to 2,300,000 g/mol and a number average molecular weight (Mn) of 500,000 g/mol to 900,000 g/mol while also satisfying the –S/R condition.

In addition, the 1,4-cis polybutadiene according to one embodiment of the present invention may have Mooney viscosity (MV) of 30 to 90 and specifically 70 to 90 at 100° C. More superior processability may be obtained when the Mooney viscosity is in the above-mentioned range.

In the present invention, Mooney viscosity may be measured using a Mooney viscometer, for example, a Large Rotor of MV2000E of Monsanto at 100° C. and Rotor Speed 2±0.02 rpm. Herein, the measurement may be made by leaving the sample used unattended for 30 minutes or longer at room temperature (23±5° C.), collecting 27±3 g thereof, and filling inside a die cavity with the sample, and operating a Platen.

More specifically, when the Mooney viscosity condition is also satisfied in addition to the –S/R, the PDI, the weight average molecular weight (Mw) and the number average molecular weight (Mn), the 1,4-cis polybutadiene according to one embodiment of the present invention is capable of enhancing mechanical properties and processability for a rubber composition in a balanced way when used in the rubber composition.

specifically the 1,4-cis polybutadiene may have, while satisfying the above-mentioned –S/R condition, PDI of or less, a weight average molecular weight (Mw) of 400,000 g/mol to 2,500,000 g/mol, a number average molecular weight (Mn) of 100,000 g/mol to 1,000,000 g/mol, and Mooney viscosity of 30 to 90 and more specifically 70 to 90 at 100° C., and even more specifically, the 1,4-cis polybutadiene may have PDI of 2.35 to 2.5, a weight average molecular weight (Mw) of 1,100,000 g/mol to 2,300,000 g/mol, a number average molecular weight (Mn) of 500,000 g/mol to 900,000 g/mol, and Mooney viscosity of 70 to 90 at 100° C.

In addition, in the 1,4-cis polybutadiene according to one embodiment of the present invention, cis bond content in the conjugated diene-based polymer measured using Fourier Transform Infrared Spectroscopy, specifically cis-1,4 bond content, may be 95% or greater and more specifically 96% or greater. When the cis-1,4 bond content in the polymer is high as above, linearity increases, and abrasion resistance and crack resistance of a rubber composition may be enhanced when being mixed to the rubber composition.

More specifically, when the 1,4-cis polybutadiene according to one embodiment of the present invention satisfying the cis-1,4 bond content condition while also satisfying the –S/R, the PDI, the weight average molecular weight (Mw) and the number average molecular weight (Mn), mechanical properties and processability are capable of being improved in a more balanced way when the 1,4-cis polybutadiene is used in a rubber composition.

Specifically, the 1,4-cis polybutadiene may have PDI of 3 or less, a weight average molecular weight (Mw) of 400,000 g/mol to 2,500,000 g/mol, a number average molecular weight (Mn) of 100,000 g/mol to 1,000,000 g/mol, and include cis-1,4 bond in 95% or greater and more specifically in 96% or greater in the polymer. More specifically, the 1,4-cis polybutadiene may have PDI of 2.35 to 2.5, a weight average molecular weight (Mw) of 1,100,000 g/mol to 2,300,000 g/mol, a number average molecular weight (Mn) of 500,000 g/mol to 900,000 g/mol, and cis-1,4 bond content of 96% or greater in the polymer.

Even more specifically, when the 1,4-cis polybutadiene according to one embodiment of the present invention satisfies the cis-1,4 bond content condition while also satisfying the –S/R, the PDI, the weight average molecular weight (Mw), the number average molecular weight (Mn) and the Mooney viscosity, mechanical properties, elasticity and processability for a rubber composition are capable of being improved in a more balanced way when the 1,4-cis polybutadiene is used in the rubber composition. Specifically, the 1,4-cis polybutadiene may have PDI of 3 or less, a weight average molecular weight (Mw) of 400,000 g/mol to 2,500,000 g/mol, a number average molecular weight (Mn) of 100,000 g/mol to 1,000,000 g/mol, Mooney viscosity of 30 to 90 at 100° C., and cis-1,4 bond content of 95% or greater in the polymer, and more specifically, may have PDI of 2.35 to 2.5, a weight average molecular weight (Mw) of 1,100,000 g/mol to 2,300,000 g/mol, a number average molecular weight (Mn) of 500,000 g/mol to 900,000 g/mol, and Mooney viscosity of 70 to 90 at 100° C., and cis-1,4 bond content of 96% or greater in the polymer.

The 1,4-cis polybutadiene according to one embodiment of the present invention having such physical properties may be prepared using a method including preparing a mixture of a molecular weight modifier and, as a monomer, 1,3-butadiene or a butadiene derivative (step 1); and polymerization reacting the mixture using a catalyst composition including a lanthanide rare earth element-containing compound, modified methylaluminoxane (MAO), a halogen compound and an aliphatic hydrocarbon-based solvent (step 2). Accordingly, another embodiment of the present invention provides a method for preparing 1,4-cis polybutadiene including each step described above, and a catalyst composition useful for preparing the 1,4-cis polybutadiene.

When examining each step, the step 1 in the method for preparing 1,4-cis polybutadiene according to one embodiment of the present invention is a step of preparing a mixture of a molecular weight modifier and a monomer.

According to the method for preparing 1,4-cis polybutadiene according to one embodiment of the present invention, a molecular weight modifier is separately mixed with a monomer instead of being introduced to a catalyst composition as in existing methods for preparing 1,4-cis polybutadiene, and therefore, the molecular weight may be quickly modified in a 1,4-cis polybutadiene production process, which leads to processability improvement.

In the step 1, organic aluminum compounds may be used as the molecular weight modifier.

Specific examples of the organic aluminum compound include trihydrocarbylaluminum such as trimethylaluminum, triethylaluminum, triisobutylaluminum, tri-n-propylaluminum, triisopropylaluminum, tri-n-butylaluminum, tri-t-butylaluminum, tri-n-pentylaluminum, trineopentylaluminum, tri-n-hexylaluminum, tri-n-octylaluminum, tris(2-ethylhexyl)aluminum, tricyclohexylaluminum, tris(1-methylcyclopentyl)aluminum, triphenylaluminum, tri-p-tolylaluminum, tris(2,6-dimethylphenyl)aluminum, tribenzylaluminum, diethylphenylaluminum, diethyl-p-tolylaluminum, diethylbenzylaluminum, ethyldiphenylaluminum, ethyldi-p-tolylaluminum or ethyldibenzylaluminum; or dihydrocarbylaluminum hydride such as dimethylaluminum hydride, diethylaluminum hydride, di-n-propylaluminum hydride, diisopropylaluminum hydride, di-n-butylaluminum hydride, diisobutylaluminum hydride (DIBAH), di-t-butylaluminum hydride, dipentylaluminum hydride, dihexylaluminum hydride, dicyclohexylaluminum hydride or dioctylaluminum hydride, and any one or a mixture of two or more of these may be used.

In addition, as the molecular weight modifier, hydrogen; or silane compounds such as trimethyl silane, triethyl silane, tributyl silane, trihexyl silane, dimethyl silane, diethyl silane, dibutyl silane or dihexyl silane may be used. The silane compound may be used alone as the molecular weight modifier, or may be mixed with the organic aluminum compound described above.

When considering superiority of improving effects by the use of a molecular weight modifier, the molecular weight modifier may be diethylaluminum hydride, diisobutylaluminum hydride (DIBAH) or a mixture thereof among the above-mentioned compounds, and more specifically, may be diisobutylaluminum hydride.

The molecular weight modifier not only modifies molecular weights but may act as a scavenger, and therefore, the amount of the molecular weight modifier used may vary depending on the amount of impurities and the amount of moisture. Specifically, in the preparation method according to one embodiment of the present invention, the content of the molecular weight modifier capable of being used in the step 1 may be from 1 mol to 100 mols and more specifically from 1 mol to 50 mols with respect to 1 mol of the lanthanide rare earth element-containing compound.

Meanwhile, in the step 1, the use of the monomer is not particularly limited as long as the monomer is commonly used in 1,4-cis polybutadiene preparation. Specifically, the monomer may be 1,3-butadiene or derivatives thereof, and more specifically, may be 1,3-butadiene, isoprene, 2,3-dimethyl-1,3-butadiene, 2-ethyl-1,3-butadiene or the like, and any one or a mixture of two or more of these may be used.

In addition, with the monomer, other monomers including conjugated diene-based monomers copolymerizable with the monomer and the conjugated diene-based monomer may be selectively used. Herein, the other monomer including the conjugated diene-based monomer additionally used may be used in proper content considering physical properties of finally prepared 1,4-cis polybutadiene.

Specifically examples of the conjugated diene-based monomer capable of being additionally used may include 2-methyl-1,3-pentadiene, 1,3-pentadiene, 3-methyl-1,3-pentadiene, 4-methyl-1,3-pentadiene, 1,3-hexadiene, 2,4-hexadiene or the like, and any one or a mixture of two or more of these may be used.

Specific examples of the other monomer capable of being additionally used may include aromatic vinyl monomers such as styrene, p-methylstyrene, a-methylstyrene, 1-vinylnaphthalene, 3-vinyltoluene, ethylvinylbenzene, divinylbenzene, 4-cyclohexylstyrene and 2,4,6-trimethylstyrene, and any one or a mixture of two or more of these may be used. The other monomer may be used in the content of 20% by weight or less with respect to the total monomer weight used in a polymerization reaction for preparing 1,4-cis polybutadiene.

In the method for preparing 1,4-cis polybutadiene according to one embodiment of the present invention, the step 2 is a step polymerization reacting the mixture prepared in the step 1 using a catalyst composition including a lanthanide rare earth element-containing compound; modified methylaluminoxane (MMAO); a halogen compound and an aliphatic hydrocarbon-based solvent.

In the step 2, the catalyst composition is a pre-mixture of a lanthanide rare earth element-containing compound, MMAO, a halogen compound and an aliphatic hydrocarbon-based solvent, and may be prepared by mixing the above-mentioned compounds using common methods.

As described above, in the method for preparing 1,4-cis polybutadiene according to one embodiment of the present invention, the catalyst composition does not include diisobutylaluminum hydride (DIBAH) unlike existing catalyst compositions for preparing a conjugated diene-based polymer, and premixing instead of preforming is carried out, and therefore, it is very advantageous in terms of a process such that blockage of polymerization reactor catalyst input line by polymers caused by existing butadiene preforming may be prevented.

Specifically, in the catalyst composition, the lanthanide rare earth element-containing compound may be a compound including any one, two or more elements among rare earth elements of atomic numbers 57 to 71 in the periodic table such as neodymium, praseodymium, cerium, lanthanum or gadolinium, and more specifically, a compound including neodymium.

In addition, the lanthanide rare earth element-containing compound may be a salt soluble in a hydrocarbon solvent such as carboxylates, alkoxides, β-diketone complexes, phosphates or phosphites of lanthanide rare earth elements, and more specifically, may be the neodyminum-containing carboxylates. The hydrocarbon solvent may be an aliphatic hydrocarbon-based solvent such as saturated aliphatic hydrocarbon having 4 to 10 carbon atoms such as butane, pentane, hexane and heptane, or saturated alicyclic hydrocarbon having 5 to 20 carbon atoms such as cyclopentane and cyclohexane.

More specifically, the lanthanide rare earth element-containing compound may be a neodymium compound of the following Chemical Formula 1:

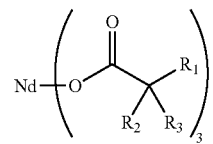

[Chemical Formula 1]

in Chemical Formula 1, $R_1$ to $R_3$ are each independently a hydrogen atom or a linear or branched alkyl group having 1 to 12 carbon atoms.

Specifically, the neodymium compound may be any one or a mixture of two or more selected from the group consisting of Nd(neodecanoate)$_3$, Nd(2-ethylhexanoate)$_3$, Nd(2,2-diethyl decanoate)$_3$, Nd(2,2-dipropyl decanoate)$_3$, Nd(2,2-dibutyl decanoate)$_3$, Nd(2,2-dihexyl decanoate)$_3$, Nd(2,2-dioctyl decanoate)$_3$, Nd(2-ethyl-2-propyl decanoate)$_3$, Nd(2-ethyl-2-butyl decanoate)$_3$, Nd(2-ethyl-2-hexyl decanoate)$_3$, Nd(2-propyl-2-butyl decanoate)$_3$, Nd(2-propyl-2-hexyl decanoate)$_3$, Nd(2-propyl-2-isopropyl decanoate)$_3$, Nd(2-butyl-2-hexyl decanoate)$_3$, Nd(2-hexyl-2-octyl decanoate)$_3$, Nd(2-t-butyl decanoate)$_3$, Nd(2,2-diethyl octanoate)$_3$, Nd(2,2-dipropyl octanoate)$_3$, Nd(2,2-dibutyl octanoate)$_3$, Nd(2,2-dihexyl octanoate)$_3$, Nd(2-ethyl-2-propyl octanoate)$_3$, Nd(2-ethyl-2-hexyl octanoate)$_3$, Nd(2,2-diethyl nonanoate)$_3$, Nd(2,2-dipropyl nonanoate)$_3$, Nd(2,2-dibutyl nonanoate)$_3$, Nd(2,2-dihexyl nonanoate)$_3$, Nd(2-ethyl-2-propyl nonanoate)$_3$ and Nd(2-ethyl-2-hexyl nonanoate)$_3$.

In addition, when considering excellent solubility for polymerization solvents without concern for oligomerization, a rate of conversion to an active catalyst species and superiority of catalytic activity improving effects obtained therefrom, the lanthanide rare earth element-containing compound may more specifically be a neodymium compound in which, in Chemical Formula 1, $R_1$ is a linear or branched alkyl group having 6 to 12 carbon atoms or 6 to 8 carbon atoms, and $R_2$ and $R_3$ are each independently a hydrogen atom or a linear or branched alkyl group having 2 to 8 carbon atoms, but $R_2$ and $R_3$ are not both hydrogen atoms at the same time. Specific examples thereof may include Nd(2,2-diethyl decanoate)$_3$, Nd(2,2-dipropyl decanoate)$_3$, Nd(2,2-dibutyl decanoate)$_3$, Nd(2,2-dihexyl decanoate)$_3$, Nd(2,2-dioctyl decanoate)$_3$, Nd(2-ethyl-2-propyl decanoate)$_3$, Nd(2-ethyl-2-butyl decanoate)$_3$, Nd(2-ethyl-2-hexyl decanoate)$_3$, Nd(2-propyl-2-butyl decanoate)$_3$, Nd(2-propyl-2-hexyl decanoate)$_3$, Nd(2-propyl-2-isopropyl decanoate)$_3$, Nd(2-butyl-2-hexyl decanoate)$_3$, Nd(2-hexyl-2-octyl decanoate)$_3$, Nd(2-t-butyl decanoate)$_3$, Nd(2,2-diethyl octanoate)$_3$, Nd(2,2-dipropyl octanoate)$_3$, Nd(2,2-dibutyl octanoate)$_3$, Nd(2,2-dihexyl octanoate)$_3$, Nd(2-ethyl-2-propyl octanoate)$_3$, Nd(2-ethyl-2-hexyl octanoate)$_3$, Nd(2,2-diethyl nonanoate)$_3$, Nd(2,2-dipropyl nonanoate)$_3$, Nd(2,2-dibutyl nonanoate)$_3$, Nd(2,2-dihexyl nonanoate)$_3$, Nd(2-ethyl-2-propyl nonanoate)$_3$ Nd(2-ethyl-2-hexyl nonanoate)$_3$, or the like, and among these, the neodymium compound may be any one or a mixture of two or more selected from the group consisting of Nd(2,2-diethyl decanoate)$_3$, Nd(2,2-dipropyl decanoate)$_3$, Nd(2,2-dibutyl decanoate)$_3$, Nd(2,2-dihexyl decanoate)$_3$ and Nd(2,2-dioctyl decanoate)$_3$.

Even more specifically, the lanthanide rare earth element-containing compound may be a neodymium compound in which, in Chemical Formula 1, $R_1$ is a linear or branched alkyl group having 6 to 8 carbon atoms, $R_2$ and $R_3$ are each independently a linear or branched alkyl group having 2 to 8 carbon atoms.

Thus, when the neodymium compound of Chemical Formula 1 includes a carboxylate ligand including an alkyl group with various lengths of 2 or more carbon atoms as a substituent at an α position, coagulation between the compounds may be blocked by inducing stereoscopic changes around the neodymium central metal, and as a result, oligomerization may be suppressed. In addition, such a neodymium compound has high solubility for polymerization solvents, and has a high rate of conversion to an active catalyst species since the ratio of neodymium located in the central part having difficulties in being converted to an active catalyst species decreases.

Furthermore, the neodymium compound of Chemical Formula 1 may have solubility of approximately 4 g or greater per 6 g of a non-polar solvent at room temperature (20±5° C.). In the present invention, solubility of the neodymium compound means a level of being clearly dissolved without turbidity. By having such high solubility, excellent catalytic activity may be obtained.

Meanwhile, in the catalyst composition, the modified methylaluminoxane functions as an alkylating agent in the catalyst composition in place of existing DIBAH. The modified methylaluminoxane is a compound substituting a methyl group of methylaluminoxane with a modification group, specifically, a hydrocarbon group having 2 to 20 carbon atoms, and may specifically be a compound of the following Chemical Formula 2:

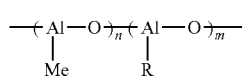

[Chemical Formula 2]

in Chemical Formula 2, R is a hydrocarbon group having 2 to 20 carbon atoms, m and n are each an integer of 2 or greater. In addition, Me in Chemical Formula 2 means a methyl group.

More specifically, R in Chemical Formula 2 may be a linear or branched alkyl group having 2 to 20 carbon atoms, a cycloalkyl group having 3 to 20 carbon atoms, an alkenyl group having 2 to 20 carbon atoms, a cycloalkenyl group having 3 to 20 carbon atoms, an aryl group having 6 to 20 carbon atoms, an aralkyl group having 7 to 20 carbon atoms, an alkylaryl group having 7 to 20 carbon atoms, an allyl group, or an alkynyl group having 2 to 20 carbon atoms, and more specifically, a linear or branched alkyl group having 2 to 10 carbon atoms such as an ethyl group, an isobutyl group, a hexyl group or an octyl group, and even more specifically an isobutyl group.

Even more specifically, the modified methylaluminoxane may be a compound substituting approximately 50 mol % or more of a methyl group of the methylaluminoxane, more specifically 50 mol % to 90 mol %, with a hydrocarbon group having 2 to 20 carbon atoms. When the content of the substituted hydrocarbon group in the modified methylaluminoxane is in the above-mentioned range, alkylation is facilitated and as a result, catalytic activity may increase.

Such modified methylaluminoxane may be prepared using common methods, and specifically, may be prepared using trimethylaluminum, and an alkylaluminum other than trimethylaluminum. Herein, the alkylaluminum may be triisobutylaluminum, triethylaluminum, trihexylaluminum, trioctylaluminum or the like, and any one or a mixture of two or more of these may be used.

With alkylaluminoxane such as methylaluminoxane (MAO) or ethylaluminoxane commonly used for conjugated diene polymer preparation, aromatic hydrocarbon-based solvents need to be used since alkylaluminoxane is not readily dissolved in aliphatic hydrocarbon-based solvents. However, aromatic hydrocarbon-based solvents have a problem of reducing reactivity, and when mixing an aromatic hydrocarbon-based solvent and an aliphatic hydrocarbon-based solvent in a catalyst system, there is a problem of reducing catalytic activity. However, in the present invention, modified methylaluminoxane capable of being readily dissolved in aliphatic hydrocarbon-based solvents is used, and accordingly, a single solvent system with an aliphatic hydrocarbon-based solvent such as hexane that is normally used as a polymerization solvent is capable of being used, which is more advantageous for a polymerization reaction. In addition, an aliphatic hydrocarbon-based solvent may facilitate catalytic activity, and reactivity may be further enhanced by such catalytic activity. As a result, molecular weights may be quickly and readily modified, and polymerization is favorably progressed even at low temperatures due to very high catalytic activity, and time for polymerization reaction may be reduced even with a small main catalyst amount.

In addition, in the catalyst composition, specific examples of the aliphatic hydrocarbon-based solvent may include a mixed solvent of a linear, branched or cyclic aliphatic hydrocarbon-based solvent having 5 to 20 carbon atoms such as n-pentane, n-hexane, n-heptane, n-octane, n-nonane, n-decane, isopentane, isohexane, isoheptane, isooctane, 2,2-dimethylbutane, cyclopentane, cyclohexane, methylcyclopentane or methylcyclohexane; or aliphatic hydrocarbon having 5 to 20 carbon atoms such as petroleum ether (or petroleum spirits) or kerosene, and any one or a mixture of two or more of these may be used. Among these, when considering excellent solubility for modified methylaluminoxane and superiority of catalytic activity improving effects resulted therefrom, the aliphatic hydrocarbon-based solvent may be a linear, branched or cyclic aliphatic hydrocarbon-based solvent having 5 to 8 carbon atoms, or a mixture thereof, and more specifically n-hexane, cyclohexane, or a mixture thereof.

Furthermore, in the catalyst composition, the types of the halogen compound are not particularly limited, and those commonly used as halogenides in diene-based polymer preparation may be used without particular limit. Specifically, the halogen compound may include elemental halogen compounds, interhalogen compounds, halogenated hydrogen, organic halides, non-metal halides, metal halides, organic metal halides or the like, and any one or a mixture of two or more of these may be used. Among these, when considering catalytic activity enhancement and superiority of reactivity improving effects resulted therefrom, any one or a mixture of two or more selected from the group consisting of organic halides, metal halides and organic metal halides may be used as the halogen compound.

More specifically, the elemental halogen compound may include diatomic molecular compounds such as fluorine ($F_2$), chlorine ($Cl_2$), bromine ($Br_2$) or iodine ($I_2$).

Specific examples of the interhalogen compound may include iodine monochloride, iodine monobromide, iodine trichloride, iodine pentafluoride, iodine monofluoride, iodine trifluoride or the like.

In addition, specific examples of the halogenated hydrogen may include hydrogen fluoride, hydrogen chloride, hydrogen bromide, hydrogen iodide or the like.

Specific examples of the organic halide may include t-butyl chloride, t-butyl bromide, allyl chloride, allyl bromide, benzyl chloride, benzyl bromide, chloro-di-phenylmethane, bromo-di-phenylmethane, triphenylmethyl chloride, triphenylmethyl bromide, benzylidene chloride, benzyliene bromide, methyltrichlorosilane, phenyltrichlorosilane, dimethyldichlorosilane, diphenyldichlorosilane, trimethylchlorosilane, benzoyl chloride, benzoyl bromide, propionyl chloride, propionyl bromide, methyl chloroformate, methyl bromoformate, iodomethane, diiodomethane, triiodomethane (also called as 'iodoform'), tetraiodomethane, 1-iodopropane, 2-iodopropane, 1,3-diiodopropane, t-butyl iodide, 2,2-dimethyl-1-iodopropane (also called as 'neopentyl iodide'), allyl iodide, iodobenzene, benzyl iodide, diphenylmethyl iodide, triphenylmethyl iodide, benzylidene iodide (also called as 'benzal iodide'), trimethylsilyl iodide, triethylsilyl iodide, triphenylsilyl iodide, dimethyldiiodosilane, diethyldiiodosilane, diphenyldiiodosilane, methyltriiodosilane, ethyltriiodosilane, phenyltriiodosilane, benzoyl iodide, propionyl iodide, methyl iodoformate or the like.

Specific examples of the non-metal halide may include phosphorous trichloride, phosphorous tribromide, phosphorous pentachloride, phosphorous oxychloride, phosphorous oxybromide, boron trifluoride, boron trichloride, boron tribromide, silicon tetrafluoride, silicon tetrachloride, silicon tetrabromide, arsenic trichloride, arsenic tribromide, selenium tetrachloride, selenium tetrabromide, tellurium tetrachloride, tellurium tetrabromide, silicon tetraiodide, arsenic triiodide, tellurium tetraiodide, boron triiodide, phosphorous triiodide, phosphorous oxyiodide, selenium tetraiodide or the like.

Specific examples of the metal halide may include tin tetrachloride, tin tetrabromide, aluminum trichloride, aluminum tribromide, antimony trichloride, antimony pentachloride, antimony tribromide, aluminum trifluoride, gallium trichloride, gallium tribromide, gallium trifluoride, indium trichloride, indium tribromide, indium trifluoride, titanium tetrachloride, titanium tetrabromide, zinc dichloride, zinc dibromide, zinc difluoride, aluminum triiodide, gallium triiodide, indium triiodide, titanium tetraiodide, zinc diiodide, germanium tetraiodide, tin tetraiodide, tin diiodide, antimony triiodide or magnesium diiodide.

Specific examples of the organic metal halide may include dimethylaluminum chloride, diethylaluminum chloride, dimethylaluminum bromide, diethylaluminum bromide, dimethylaluminum fluoride, diethylaluminum fluoride, methylaluminum dichloride, ethylaluminum dichloride, methylaluminum dibromide, ethylaluminum dibromide, methylaluminum difluoride, ethylaluminum difluoride, methylaluminum sesquichloride, ethylaluminum sesquichloride, isobutylaluminum sesquichloride, methylmagnesium chloride, methylmagnesium bromide, ethylmagnesium chloride, ethylmagnesium bromide, n-butylmagnesium chloride, n-butylmagnesium bromide, phenylmagnesium chloride, phenylmagnesium bromide, benzylmagnesium chloride, trimethyltin chloride, trimethyltin bromide, triethyltin chloride, triethyltin bromide, di-t-butyltin dichloride, di-t-butyltin dibromide, di-n-butyltin dichloride, di-n-butyltin dibromide, tri-n-butyltin chloride, tri-n-butyltin bromide, methylmagnesium iodide, dimethylaluminum iodide, diethylaluminum iodide, di-n-butylaluminum iodide, diisobutylaluminum iodide, di-n-octylaluminum iodide, methylaluminum diiodide, ethylaluminum diiodide, n-butylaluminum diiodide, isobutylaluminum diiodide, methylaluminum sesquiiodide, ethylaluminum sesquiiodide, isobutylaluminum sesquiiodide, ethylmagnesium iodide, n-butylmagnesium iodide, isobutylmagnesium iodide, phenylmagnesium iodide, benzylmagnesium iodide, trimethyltin iodide, triethyltin iodide, tri-n-butyltin iodide, di-n-butyltin diiodide, di-t-butyl tin diiodide or the like.

The catalyst composition according to one embodiment of the present invention may include the above-mentioned constituents in optimum content so as to exhibit more superior catalytic activity in a polymerization reaction for forming 1,4-cis polybutadiene.

The catalyst composition may include the lanthanide rare earth element-containing compound in an amount of 0.01 mmol to 0.25 mmol, specifically in 0.02 mmol to 0.20 mmol and more specifically in 0.02 mmol to 0.10 mmol with respect to 100 g of the monomer.

In addition, the catalyst composition may include the modified methylaluminoxane in a molar ratio of 5 to 200 and more specifically in a molar ratio of 10 to 100 with respect to 1 mol of the lanthanide rare earth element-containing compound.

Furthermore, the catalyst composition may include the halogen compound in a molar ratio of 1 to 10 and more specifically in a molar ratio of 2 to 6 with respect to 1 mol of the lanthanide rare earth element-containing compound.

In addition, the catalyst composition may include the aliphatic hydrocarbon-based solvent in a molar ratio of 20 to 20,000 and more specifically in a molar ratio of 100 to 1,000 with respect to 1 mol of the lanthanide rare earth element-containing compound.

More specifically, when considering superiority of catalytic activity for a polymerization reaction of a conjugated diene-based polymer, the catalyst composition according to one embodiment of the present invention may include the modified methylaluminoxane in 5 mols to 200 mols, the halogen compound in 1 mol to 10 mols and the aliphatic hydrocarbon-based solvent in 20 mols to 20,000 mols with respect to 1 mol of the lanthanide rare earth element-containing compound.

According to another embodiment of the present invention, the catalyst composition may include the lanthanide rare earth element-containing compound in an amount of 0.01 mmol to 0.25 mmol, the modified methylaluminoxane in 0.1 mmol to 25.0 mmol, the halogen compound in 0.02 mmol to 1.5 mmol and the aliphatic hydrocarbon-based solvent in 10 mmol to 180 mmol with respect to 100 g of the monomer.

More specifically, the catalyst composition includes the lanthanide rare earth element-containing compound in an amount of 0.01 mmol to 0.05 mmol, the modified methylaluminoxane in 0.1 mmol to 5.0 mmol, the halogen compound in 0.03 mmol to 0.10 mmol, and the aliphatic hydrocarbon-based solvent in 10 mmol to 180 mmol with respect to 100 g of the monomer.

When considering superiority of catalytic activity for a polymerization reaction of 1,4-cis polybutadiene, the catalyst composition according to one embodiment of the present invention is a pre-mixture including the lanthanide rare earth element-containing compound in 0.01 mmol to 0.25 mmol, the modified methylaluminoxane in 0.05 mmol to 50.0 mmol, the halogen compound in 0.01 mmol to 2.5 mmol and the aliphatic hydrocarbon-based solvent in 2 mmol to 200 mmol or 5 mmol to 200 mmol with respect to 100 g of the monomer, and herein, the lanthanide rare earth element-containing compound includes a neodymium compound in which, in Chemical Formula 1, $R_1$ is a linear or branched alkyl group having 6 to 12 carbon atoms, and $R_2$ and $R_3$ are each independently a hydrogen atom or a linear or branched alkyl group having 2 to 6 carbon atoms, but $R_2$ and $R_3$ are not both hydrogen atoms at the same time, and the modified methylaluminoxane is a compound substituting approximately 50 mol % or more of a methyl group of the methylaluminoxane with a hydrocarbon group having 2 to 20 carbon atoms, and the aliphatic hydrocarbon-based solvent includes any one or a mixture of two or more selected from the group consisting of linear, branched and cyclic aliphatic hydrocarbon-based solvents having 5 to 8 carbon atoms.

In addition, mixing of the lanthanide rare earth element-containing compound, the modified methylaluminoxane, the halogen compound and the aliphatic hydrocarbon-based solvent such as above may be carried out using common methods. Herein, the mixing may be carried out in a temperature range of 0° C. to 60° C. in order to facilitate active catalyst species production, and a heat treatment process may be combined for satisfying the above-mentioned temperature condition. More specifically, a mixed process including the steps of mixing the lanthanide rare earth element-containing compound, the modified methylaluminoxane and the aliphatic hydrocarbon-based solvent in the above-mentioned composition, first heat treating the result at a temperature of 10° C. to 60° C., and carrying out a second heat treatment in a temperature range of 0° C. to 60° C. by introducing the halogen compound to the mixture resultantly obtained may be carried out.

The catalyst composition having a composition as described above may exhibit catalytic activity of 10,000 kg[polymer]/mol[Nd]h during polymerization of 5 minutes to 60 minutes in a temperature range of 20° C. to 90° C. The catalytic activity in the present invention is a value obtained from a molar ratio of the lanthanide rare earth element-containing compound, more specifically the neodymium compound of Chemical Formula 1, introduced with respect to the total yield of the prepared diene-based polymer.

Meanwhile, during the polymerization reaction in the step 2, a reaction terminating agent such as polyoxyethylene glycol phosphate, an antioxidant such as 2,6-di-t-butylparacresol, and additives such as a chelating agent, a dispersion agent, a pH controlling agent, a deoxidizer or an oxygen scavenger commonly used for facilitating solution polymerization may be further used selectively.

In addition, the polymerization reaction in the step 2 may be carried out in a temperature range of 20° C. to 90° C., and particularly, a 100% conversion rate of polymers is capable of being accomplished in a short time even at a low temperature of 20° C. to 30° C. When the temperature exceeds 90° C. in the polymerization reaction, the polymerization reaction is difficult to be sufficiently controlled, and there is concern that cis-1,4 bond content of the produced diene-based polymer may decrease. When the temperature is less than 20° C., there is concern that polymerization reaction rate and efficiency may decrease.

Furthermore, according to the preparation method according to one embodiment of the present invention, the polymerization reaction may be carried out for 5 minutes to 60 minutes until the reaction reaches 100% conversion to the conjugated diene-based polymer, and specifically, may be carried out for 10 minutes to 30 minutes.

In addition, after the reaction is complete, the prepared 1,4-cis polybutadiene may be obtained by adding lower alcohols such as methyl alcohol or ethyl alcohol, or steam for precipitation. Accordingly, the method for preparing 1,4-cis polybutadiene according to one embodiment of the present invention may further include precipitation and separation processes for a conjugated diene-based polymer prepared after the polymerization reaction. Herein, filtering, separating and drying processes for the conjugated diene-based polymer may be carried out using common methods.

According to the preparation method such as above, 1,4-cis polybutadiene, specifically, a neodymium-catalyzed 1,4-cis polybutadiene including an active organic metal site derived from a catalyst including the lanthanide rare earth element-containing compound, more specifically the neodymium compound of Chemical Formula 1, and even more specifically, neodymium-catalyzed 1,4-cis polybutadiene including a 1,3-butadiene monomer unit is produced. In addition, the conjugated diene-based polymer may be 1,4-cis polybutadiene formed only with a 1,3-butadiene monomer.

In addition, 1,4-cis polybutadiene prepared using the above-mentioned preparation method has excellent physical properties including high linearity as described above. Consequently, another embodiment of the present invention provides a rubber composition including the 1,4-cis polybutadiene.

Specifically, the rubber composition may include the 1,4-cis polybutadiene in 10% by weight to 100% by weight and a rubber component in 0 to 90% by weight. When the content of the 1,4-cis polybutadiene is less than 10% by weight, effects of improving abrasion resistance, crack resistance and ozone resistance of the rubber composition may be insignificant.

In the rubber composition, the rubber component may be specifically natural rubber (NR); or synthetic rubber such as a styrene-butadiene copolymer (SBR), hydrogen-added SBR, polybutadiene (BR) having low cis-1,4-bond content, hydrogen-added BR, polyisoprene (IR), butyl rubber (IIR), ethylene-propylene rubber, ethylene-propylene diene rubber, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), polysulfide rubber, acrylic rubber, urethane rubber, silicone rubber or epichlorohydrin rubber, and any one or a mixture of two or more of these may be used.

In addition, the rubber composition may further include a filler in 10 parts by weight or greater with respect to 100 parts by weight of the rubber component. Herein, the filler may be carbon black, starch, silica, aluminum hydroxide, magnesium hydroxide, clay (hydrated aluminum silicate) and the like, and any one or a mixture of two or more of these may be used.

Furthermore, the rubber composition may further include, in addition to the rubber component and the filler described above, compounding agents commonly used in a rubber industry such as a vulcanizing agent, a vulcanization accelerator, an antiaging agent, an antiscorching agent, a softner, zinc oxide, stearic acid or silane coupling agent by properly selecting and mixing them within a range that does not undermine an object of the present invention.

Specifically, such a rubber composition is useful for preparing various molded rubber articles such as automobiles, trucks (tracks), tires for buses (for example, tire treads, side walls, sub-treads, bead fillers, brake members and the like), elastic components of a tire stock, O-rings, profiles, gaskets, films, hoses, belts, shoe soles, cushion rubber or window seals. Particularly, by including a conjugated diene-based polymer having high linearity with a –S/R value of 1 or greater at 100° C., resistance properties, particularly rolling resistance decreases, and significantly improved fuel efficiency properties are obtained, and as a result, the rubber composition may be useful in tires requiring low resistance properties and excellent fuel efficiency properties.

Hereinafter, the present invention will be described in detail with reference to examples in order to specifically describe the present invention. However, the examples according to the present invention may be modified to various other forms, and the scope of the present invention is not to be interpreted to be limited to the examples described below. The examples of the present invention are provided in order to more completely describe the present invention for those skilled in the art.

[Preparation of Neodymium Compound]

PREPARATION EXAMPLE 1

Synthesis of Nd(2,2-dihexyl decanoate)$_3$

To a 50 ml round flask having 0.35 g (1.0 mmol) of 2,2-dihexyl decanoic acid therein, 10 ml of ethanol was added, and the result was stirred for 10 minutes at room temperature (20±5° C.). 1.0 ml of a 1.0 M aqueous sodium hydroxide solution (1.0 mmol) was added to the mixed solution obtained as a result, and the result was stirred for 1 hour at room temperature to prepare a first mixed solution.

A second mixed solution was prepared by placing 0.125 g (0.35 mmol) of neodymium chloride hydrate in a 250 ml round flask, and then adding 20 ml of hexane and 10 ml of ethanol thereto to dissolve the neodymium compound.

The first mixed solution was introduced to a dropping funnel and was dropped to the second mixed solution at room temperature to prepare a third mixed solution. After completing the addition, the result was stirred for 15 hours at room temperature.

The third mixed solution was vacuum distilled to remove all the solvent, 50 ml of hexane and 50 ml of distilled water were added to the third mixed solution, the result was introduced to a separatory funnel, and the organic layer was extracted repeating 3 times. Sodium sulfate was added to the collected organic layer, the result was stirred for 10 minutes at room temperature, and then the solution obtained from filtration was removed by vacuum distillation. As a result, 0.38 g (yield 94%) of title compound (I), which is yellow and blue solid, dissolved in hexane was obtained.

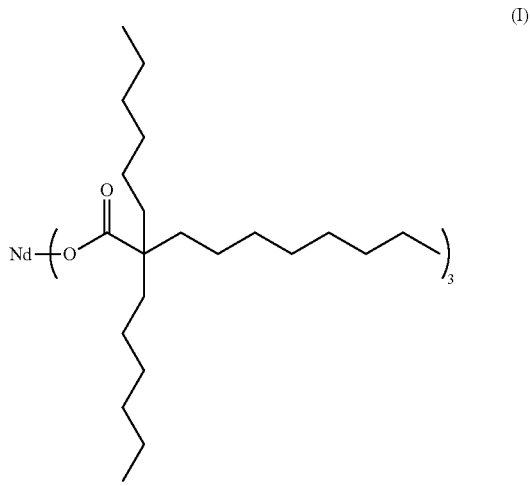

(I)

FT-IR: υ 953, 2921, 2852, 1664, 1557, 1505, 1457, 1412, 1377, 1311, 1263 cm$^{-1}$

PREPARATION EXAMPLE 2

Synthesis of Nd(neodecanoate)$_3$

To a 100 ml round flask having 4.32 g (25 mmol) of neodecanoic acid therein, 100 ml of ethanol was added, and the result was stirred for 10 minutes at room temperature (20±5° C.). 25 ml of a 1.0 M aqueous sodium hydroxide solution (25 mmol) was added to this solution, and the result was stirred for 1 hour at room temperature to prepare a first mixed solution.

A second mixed solution was prepared by placing 3.0 g (8.3 mmol) of neodymium chloride hydrate in a 500 ml round flask, and then adding 150 ml of hexane and 100 ml of ethanol thereto to dissolve the neodymium compound.

The first mixed solution was introduced to a dropping funnel and was dropped to the second mixed solution at room temperature to prepare a third mixed solution. After completing the addition, the result was stirred for 15 hours at room temperature.

The third mixed solution was vacuum distilled to remove all the solvent, 100 ml of hexane and 100 ml of distilled water were added to the third mixed solution, the result was introduced to a separatory funnel, and the organic layer was extracted repeating 3 times. Sodium sulfate was added to the collected organic layer, the result was stirred for 10 minutes at room temperature, and then the solution obtained from filtration was removed by vacuum distillation. As a result, 5.3 g (yield: 96%) of a title compound (II), which is purple solid, was obtained.

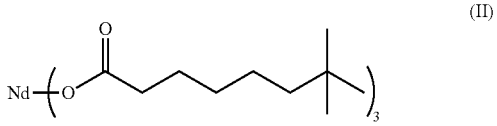 (II)

FT-IR: υ 956, 2926, 2872, 1512, 1462, 1411, 1375, 1181, 641 cm$^{-1}$

[Preparation of 1,4-Cis Polybutadiene]

EXAMPLE 1

Step (i): Preparation of Molecular Weight Modifier and Monomer Mixture

Vacuum and nitrogen were alternately applied to a completely dried 10 L high pressure reactor, and an atmospheric pressure (1±0.05 atm) state was made by filling the reactor with nitrogen again. To this high pressure reactor, hexane (2086.4 g) and 1,3-butadiene (250 g) were added and mixed, and first heat treatment was carried out for approximately 10 minutes at 70° C. Diisobutylaluminum hydride (DIBAH) was added and mixed to this high pressure reactor in an amount listed in the following Table 1, the resultant mixed solution was second heat treated for approximately 2 minutes at approximately 70° C. to prepare a mixture of a molecular weight modifier and a monomer.

Step (ii): Polymerization Reaction

The neodymium compound of Preparation Example 1, modified methylaluminoxane (MMAO)(MISC MAO, Lot: 9578-110-3, Albemarle Corporation, Al content in isoheptane=8.6% by weight) and hexane were premixed in amounts listed in the following Table 1, and then the result was heat treated for minutes at 50° C. To the resultant mixture, diethylaluminum chloride (DEAC) was added in an amount listed in the following Table 1, and the result was heat treated for 10 minutes at 26° C. to prepare a catalyst composition.

To the mixture of the molecular weight modifier and the monomer prepared in the step (i), the catalyst composition was injected, and a polymerization reaction was carried out for 40 minutes at 70° C. to obtain 1,4-cis polybutadiene.

EXAMPLE 2

1,4-Cis polybutadiene was prepared in the same manner as in Example 1 except that the neodymium compound prepared in Preparation Example 1, the MMAO, the hexane, the DIBAH and the DEAC were used in amounts listed in the following Table 1.

EXAMPLES 3 and 4

1,4-Cis polybutadiene was prepared in the same manner as in Example 1 except that the neodymium compound prepared in Preparation Example 2 was used instead of the neodymium compound prepared in Preparation Example 1, and the neodymium compound of Preparation Example 2, the MMAO, the hexane, the DIBAH and the DEAC were used in amounts listed in the following Table 1.

EXAMPLES 5 to 7

1,4-Cis polybutadiene was prepared in the same manner as in Example 1 except that the neodymium compound prepared in Preparation Example 2 was used instead of the neodymium compound prepared in Preparation Example 1, and the polymerization reaction was carried out for approximately 40 minutes at a polymerization reaction temperature of 30° C. using the neodymium compound of Preparation Example 2, the MMAO, the hexane, the DIBAH and the DEAC in amounts listed in the following Table 2.

COMPARATIVE EXAMPLE 1

Vacuum and nitrogen were alternately applied to a completely dried 10 L high pressure reactor, and an atmospheric pressure state was made by filling the reactor with nitrogen again. To this high pressure reactor, hexane (2086.4 g) and 1,3-butadiene (250 g) were added and mixed, and first heat treatment was carried out for approximately minutes at 70° C. A solution mixing the neodymium compound of Preparation Example 1, DIBAH and DEAC in amounts listed in the following Table 1 was added to this high pressure reactor, and the result was polymerization reacted for 30 minutes at 70° C. to prepare 1,4-cis polybutadiene.

COMPARATIVE EXAMPLE 2

1,4-Cis polybutadiene was prepared in the same manner as in Comparative Example 1 except that the neodymium compound prepared in Preparation Example 2 was used instead of the neodymium compound prepared in Preparation Example 1, and the neodymium compound of Preparation Example 2, the hexane, the DIBAH and the DEAC were used in amounts listed in the following Table 1, and the reaction was carried out under a condition listed in Table 1.

COMPARATIVE EXAMPLES 3 and 4

1,4-Cis polybutadiene was prepared in the same manner as in Comparative Example 1 except that the neodymium compound prepared in Preparation Example 2 was used instead of the neodymium compound prepared in Preparation Example 1, and the neodymium compound of Preparation Example 2, the hexane, the DIBAH and the DEAC were used in amounts listed in the following Table 2, and the reaction was carried out under a condition listed in Table 2.

TEST EXAMPLE 1

Evaluation on Conversion Rate and Catalytic Activity

After completing the polymerization reaction for preparing 1,4-cis polybutadiene in the examples and the comparative examples, some of the reaction solution was taken to measure a conversion rate, and catalytic activity was calculated based on the conversion rate.

In detail, the conversion rate was calculated using a ratio of a value measuring the mass of some of the reaction solution taken after completing the polymerization reaction, and a value measuring the mass of polybutadiene remaining after removing all the hexane solvent and residual butadiene by heating the some of the polymer for 10 minutes at 120° C.

In addition, catalytic activity was calculated based on the conversion rate using the mass of the produced polybutadiene, the number of mols of the neodymium compound used in the polymerization reaction, and the polymerization time. The results are shown in the following Tables 1 and 2.

TEST EXAMPLE 2

Evaluation on Physical Property

Physical properties of each 1,4-cis polybutadiene prepared in the examples and the comparative examples were measured as follows, and the results are shown in the following Tables 1 and 2.

1) Weight Average Molecular Weight (Mw), Number Average Molecular Weight (Mn) and Polydispersity (PDI)

The 1,4-cis polybutadiene prepared in the examples and the comparative examples was each dissolved for 30 minutes in tetrahydrofuran (THF) under a condition of 40° C., and was loaded and passed through gel permeation chromatography (GPC). Herein, two PLgel Olexis (trade name) columns and a PLgel mixed-C column manufactured by Polymer Laboratories were combined and used as the column. In addition, mixed bed-type columns were all used as the newly replaced column, and polystyrene was used as a gel permeation chromatography (GPC) standard material.

2) Mooney Viscosity and −S/R Value

For the 1,4-cis polybutadiene prepared in the examples and the comparative examples, Mooney viscosity (MV) was measured using a Large Rotor of MV2000E manufactured by Monsanto under a condition of Rotor Speed 2±0.02 rpm at 100° C. Herein, the used sample was left unattended for 30 minutes or longer at room temperature (23±5° C.), 27±3 g thereof was collected, and inside a die cavity is filled with the sample, and Mooney viscosity was measured while operating a Platen and applying Torque.

In addition, changes in the Mooney viscosity appearing while releasing Torque were observed when measuring the Mooney viscosity, and the −S/R value was determined from the slope.

3) Cis-1,4 Bond Content

For the 1,4-cis polybutadiene prepared in the examples and the comparative examples, Fourier Transform Infrared Spectroscopy analyses were carried out, and cis-1,4 bond content in the 1,4-cis polybutadiene was obtained from the results.

TABLE 1

| | Molecular Weight Modifier- Containing Mixture | Catalyst Composition Preparation | | | | | Polymerization Reaction | | Conversion |
|---|---|---|---|---|---|---|---|---|---|
| | Preparation[1] DIBAH (mmol) | Nd-Based Compound (mmol) | MMAO (mmol) | DEAC (mmol) | Hexane (mmol) | DIBAH (mmol) | Temperature (° C.) | Time (min) | Rate (%) |
| Example 1 | 0.25 | Preparation Example 1 0.08 | 8.0 | 0.18 | 80 | — | 70 | 10 | 100 |
| Example 2 | 0.66 | Preparation Example 1 0.08 | 4.0 | 0.18 | 80 | — | 70 | 10 | 100 |
| Example 3 | 1.0 | Preparation Example 2 0.04 | 1.2 | 0.09 | 40 | — | 70 | 10 | 100 |
| Example 4 | 1.0 | Preparation Example 2 0.04 | 0.8 | 0.09 | 40 | — | 70 | 10 | 100 |
| Comparative Example 1 | — | Preparation Example 1 0.24 | — | 0.55 | 120 | 3.0 | 70 | 30 | 88 |
| Comparative Example 2 | — | Preparation Example 2 0.24 | — | 0.55 | 120 | 3.0 | 70 | 30 | 86 |

| | Physical Property Evaluation | | | | | | |
|---|---|---|---|---|---|---|---|
| | Catalytic Activity (kg[polymer]/ mol[Nd] · h) | Mn (×10³ g/mol) | Mw (×10³ g/mol) | PDI | MV | −S/R | Cis-1,4 Bond Content (%) |
| Example 1 | 13,194 | 8.9 | 22.2 | 2.5 | 88.6 | 1.0521 | 96.8 |
| Example 2 | 13,194 | 6.7 | 15.9 | 2.38 | 75.7 | 1.0456 | 96.2 |
| Example 3 | 26,338 | 4.3 | 9.9 | 2.31 | 43.5 | 1.0423 | 98.4 |
| Example 4 | 26,338 | 4.2 | 10.2 | 2.41 | 59.8 | 1.0786 | 98.3 |
| Comparative Example 1 | 733 | 1.9 | 6.2 | 3.24 | 46.0 | 0.6529 | 96.4 |
| Comparative Example 2 | 717 | 2.1 | 9.0 | 4.34 | 45.5 | 0.6556 | 97.8 |

TABLE 2

| | Molecular Weight Modifier-Containing Mixture | Catalyst Composition Preparation | | | | | Polymerization | | Conversion |
|---|---|---|---|---|---|---|---|---|---|
| | Preparation[1] | Nd-Based | | | | | Reaction | | |
| | DIBAH (mmol) | Compound (mmol) | MMAO (mmol) | DEAC (mmol) | Hexane (mmol) | DIBAH (mmol) | Temperature (° C.) | Time (min) | Rate (%) |
| Example 5 | 0.92 | Preparation Example 2 0.08 | 8.0 | 0.18 | 80 | — | 30 | 40 | 100 |
| Example 6 | 0.87 | Preparation Example 2 0.08 | 0.8 | 0.18 | 80 | — | 30 | 40 | 100 |
| Example 7 | 0.88 | Preparation Example 2 0.08 | 8.0 | 0.18 | 80 | — | 30 | 40 | 100 |
| Comparative Example 3 | — | Preparation Example 2 0.20 | — | 0.46 | 100 | 2.04 | 70 | 60 | 96 |
| Comparative Example 4 | — | Preparation Example 2 0.20 | — | 0.46 | 100 | 1.82 | 70 | 60 | 91 |

| | Physical Property Evaluation | | | | | | |
|---|---|---|---|---|---|---|---|
| | Catalytic Activity (kg[polymer]/ mol[Nd] · h) | Mn (×10³ g/mol) | Mw (×10³ g/mol) | PDI | MV | −S/R | Cis-1,4 Bond Content (%) |
| Example 5 | 4,688 | 3.1 | 7.4 | 2.85 | 39.5 | 1.0306 | 96.0 |
| Example 6 | 4,688 | 3.2 | 8.0 | 2.46 | 46.1 | 1.0122 | 95.6 |
| Example 7 | 4,688 | 3.4 | 8.3 | 2.41 | 50.5 | 1.0446 | 96.1 |
| Comparative Example 3 | 1,200 | 2.0 | 6.3 | 3.06 | 33.5 | 0.8563 | 96.5 |
| Comparative Example 4 | 1,318 | 2.4 | 7.7 | 3.28 | 43.8 | 0.8548 | 97.4 |

In Tables 1 and 2, preparation of a mixture containing a molecular weight modifier of 1) means preparation of a mixture by mixing a molecular weight modifier and a diene-based monomer.

Table 1 compares polymer conversion rates, catalytic activity, and cis-1,4 bond content in the prepared polymers, molecular weight distribution and linearity depending on the content of the MMAO and the DIBAH, and the order of the DIBAH introduction.

As can be seen from Table 1, the polymers of Examples 1 to 4 exhibited significantly enhanced polymer conversion rates and catalytic activity.

When specifically examined, in Examples 1 to 4, the polymerization time was reduced to ⅓ at the same polymerization temperature even when using the Nd-based main catalyst compound in a small amount of approximately ⅙ to ⅓ compared to Comparative Examples 1 and 2. In addition, in Examples 1 to 4, a 100% polymer conversion rate was obtained even when reducing the amount of the main catalyst and the polymerization time. Meanwhile, in Comparative Examples 1 and 2, low polymer conversion rates of approximately 86% to 88% were obtained despite that the amount of the main catalyst increased by 3 times to 6 times, and the polymerization time increased by 3 times compared to Examples 1 to 4.

In addition, in Examples 1 to 4, catalytic activity was enhanced up to 15 times to 35 times when compared to Comparative Examples 1 and 2.

Furthermore, the 1,4-cis polybutadiene prepared in Examples 1 to 4 exhibited narrower molecular weight distribution compared to Comparative Examples 1 and 2. Specifically, whereas the 1,4-cis polybutadiene of Examples 1 to 4 had PDI in a range of 2.3 to 2.5 with a molecular weight distribution range of 2.5 or less, the polymers of Comparative Examples 1 and 2 had PDI of 3.24 and 4.34, respectively, and exhibited significantly increased molecular weight distribution compared to Examples 1 to 4.

In addition, Table 2 compares polymer conversion rates, catalytic activity, and cis-1,4 bond content in the prepared 1,4-cis polybutadiene, molecular weight distribution and linearity depending on the order of the DIBAH introduction while varying the DIBAH content and the polymerization temperature.

Specifically, as can be seen from Table 2, Examples 5 to 7 had very high catalytic activity, and polymerization was readily carried out in a short period of time even at a low temperature (30° C.). Meanwhile, in Comparative Examples 3 and 4, the polymerization conversion rate did not reach 100% even when polymerization was carried out for 60 minutes at 70° C.

In addition, the 1,4-cis polybutadiene prepared in Examples 5 to 7 had −S/R of 1 or greater, a value increased by 20% or greater compared to Comparative Examples 3 and 4. From this result, it may be predicted that the 1,4-cis polybutadiene of Example 5 to 7 had very high linearity, and as a result, when used in tires, rolling resistance declines and fuel efficiency properties is capable of being enhanced.

TEST EXAMPLE 3

Evaluation on Physical Property of Rubber Composition

In order to evaluate improving effects of a rubber composition including the 1,4-cis polybutadiene, a rubber composition including the 1,4-cis polybutadiene prepared in Example 3 as raw material rubber was prepared, and mechanical properties, resistance properties and the like for the prepared rubber composition were evaluated.

In detail, a rubber composition was prepared in accordance with the ASTM 3187-00 by mixing the mixture listed in the following Table 3 for 8 minutes (premixing 1 minute, compounding 7 minutes) at 50° C. under a condition of 50 rpm using a Haake rheomix equipped with a banbury rotor. Herein, for comparison, a rubber composition was prepared in the same manner as above using 1,4-cis polybutadiene (NdBR-40™, manufactured by Kumho Petrochemical) prepared using a neodymium-based catalyst used in traditional tire manufacture as raw material rubber, and used (Comparative Example 5).

TABLE 3

| | | Example 3 Rubber Composition | | Comparative Example 5 Rubber Composition | |
|---|---|---|---|---|---|
| | | Parts by Weight | Introduced Amount (g) | Parts by Weight | Introduced Amount (g) |
| Raw Material Rubber | Polymer of Example 3 | 100 | 140 | — | — |
| | Polymer of Comparative Example 5[1)] | — | — | 100 | 140 |
| Vulcanization Accelerator | Zinc Oxide | 3 | 4.2 | 3 | 4.2 |
| Vulcanizing Agent | Sulfur | 1.5 | 2.1 | 1.5 | 2.1 |
| Dispersion Agent | Stearic Acid | 1 | 1.4 | 1 | 1.4 |
| Reinforcing Filler | CB[2)] | 40 | 56 | 40 | 56 |
| Vulcanization Accelerator | TBBS[3)] | 0.7 | 0.98 | 0.7 | 0.98 |

1) to 3) in Table 3 are as follows:
1) Polymer of Comparative Example 5: NdBR-40™, manufactured by Kumho Petrochemical
2) CB: Carbon Black (N330™, manufactured by Showa Cabot K.K)
3) TBBS: N-tert-butyl-2-benzothiazole sulfenamide Physical properties of the rubber compositions prepared above were measured as follows, and shown in the following Table 4 together with physical properties of each polymer.

1) Modulus

The rubber compositions prepared in Example 3 and Comparative Example 5 were each vulcanized for 45 minutes at 145° C., and then Modulus at 10% elongation, 100% elongation, and 300% elongation (M-10%, M-100% and M-300%) was each measured.

2) Tensile Strength (TS, kg·f/cm$^2$)

The rubber compositions prepared in Example 3 and Comparative Example 5 were each vulcanized at 145° C., and then tensile strength of the vulcanized material was measured.

3) Elongation (%)

The rubber compositions prepared in Example 3 and Comparative Example 5 were each vulcanized for 45 minutes at 145° C., and elongation of the vulcanized material was measured.

4) Tan δ Property

A tan δ property, a most important property in fuel efficiency properties, was measured through a temperature sweep test while raising the temperature by 2° C./minute in a 0° C. to 60° C. range at frequency 10 Hz, Prestrain 5% and Dynamic Strain 3% using DMTS 500N manufactured by NETZCH GABO Instruments GMbH of Germany.

As a low temperature tan δ value at 0° C. increases, wet skid resistance is more superior, and as a high temperature tan δ value at 60° C. decreases, hysteresis loss is smaller and rolling resistance of tires, that is, a fuel efficiency property, is more superior.

In addition, index values of each measured physical property show relative ratios with a measured physical property value in a rubber composition using CB24 manufactured by Lanxess as a reference material instead of the raw material rubber as 100 when preparing the rubber composition preparation.

TABLE 4

| | Example 3 | Comparative Example 5 |
|---|---|---|
| Main Catalyst | Nd Compound of Preparation Example 2 | Nd(neodecanoate)$_3$•(neodecanoic acid) (NDH) |
| Cis-1,4 Bond Content (%) | 98.4 | 94.7 |
| Mn (×10$^5$ g/mol) | 4.3 | 1.70 |
| Mw (×10$^5$ g/mol) | 9.9 | 7.30 |
| Mw/Mn | 2.31 | 4.36 |
| ML1 + 4(@100° C.) | 43.5 | 42.4 |
| −S/R | 1.0423 | 0.6228 |
| M-10% | 6.9 | 3.7 |
| M-100% | 22 | 18 |
| M-300% | 94 | 87 |
| M-300% Index | 92 | 89 |
| Tensile Stress | 146 | 157 |
| Tensile Stress Index | 101 | 96 |
| Elongation | 402 | 446 |
| Elongation Index | 106 | 105 |
| Tanδ @ 0° C. | 0.178 | 0.199 |
| Tanδ @ 0° C. Index | 105 | 113 |
| Tanδ @ 60° C. | 0.135 | 0.146 |
| Tanδ @ 60° C. Index | 95 | 91 |

As a result, the rubber composition including the 1,4-cis polybutadiene of Example 3 according to the present invention exhibited excellent mechanical properties and resistance properties compared to Comparative Example 5, and particularly, it was identified that excellent fuel efficiency properties were obtained from a rolling resistance improving effect.

What is claimed is:

1. 1,4-cis polybutadiene, which has a −S/R (stress/relaxation) value of 1 or greater at 100° C.,
   wherein the conjugated diene-based polymer has a weight average molecular weight (Mw) of 740,000 g/mol to 2,500,000 g/mol, and a number average molecular weight (Mn) of 310,000 g/mol to 1,000,000 g/mol,
   which is obtained by preparing a mixture of a molecular weight modifier and, as a monomer, 1,3-butadiene or a butadiene derivative prior to polymerization;
   and polymerization reacting the mixture using a catalyst composition, wherein the catalyst composition includes a lanthanide rare earth element-containing compound.

2. The 1,4-cis polybutadiene of claim 1, which has a ratio (Mw/Mn) of a weight average molecular weight (Mw) to a number average molecular weight (Mn) of 3 or less.

3. The 1,4-cis polybutadiene of claim 1, which has Mooney viscosity of 30 to 90 at 100° C.

4. The 1,4-cis polybutadiene of claim 1, which has 95% or higher cis-1,4 bond content.

5. The 1,4-cis polybutadiene of claim 1, wherein the catalyst composition further includes a modified methylaluminoxane, a halogen compound and an aliphatic hydrocarbon-based solvent.

6. The 1,4-cis polybutadiene of claim 1, wherein the molecular weight modifier includes any one or a mixture of two or more selected from the group consisting of trihydrocarbylaluminum, dihydrocarbylaluminum hydride, hydrogen and silane compounds.

7. The 1,4-cis polybutadiene of claim 1, wherein the molecular weight modifier is used in a molar ratio of 1 to 100 with respect to 1 mol of the lanthanide rare earth element-containing compound.

8. The 1,4-cis polybutadiene of claim 5, wherein the catalyst composition is a pre-mixture of the lanthanide rare earth element-containing compound, the modified methylaluminoxane, the halogen compound and the aliphatic hydrocarbon-based solvent.

9. The 1,4-cis polybutadiene of claim 5, wherein the catalyst composition includes the lanthanide rare earth element-containing compound in an amount of 0.01 mmol to 0.25 mmol with respect to 100 g of the monomer.

10. The 1,4-cis polybutadiene of claim 5, wherein the catalyst composition includes the lanthanide rare earth element-containing compound in 0.01 mmol to 0.25 mmol, the modified methylaluminoxane in 0.05 mmol to 50.0 mmol, the halogen compound in 0.01 mmol to 2.5 mmol and the aliphatic hydrocarbon-based solvent in 5 mmol to 200 mmol with respect to 100 g of the monomer.

11. The 1,4-cis polybutadiene of claim 5, wherein the catalyst composition includes the lanthanide rare earth element-containing compound and the modified methylaluminoxane in a molar ratio of 1.0:5.0 to 1.0:200.

12. The 1,4-cis polybutadiene of claim 5, wherein the catalyst composition includes the modified methylaluminoxane in 5 mols to 200 mols, the halogen compound in 1 mol to 10 mols and the aliphatic hydrocarbon-based solvent in 20 mols to 20,000 mols with respect to 1 mol of the lanthanide rare earth element-containing compound.

13. The 1,4-cis polybutadiene of claim 1, wherein the lanthanide rare earth element-containing compound includes a neodymium compound of the following Chemical Formula 1:

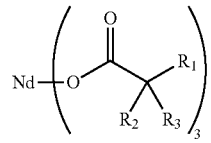

[Chemical Formula 1]

wherein, in Chemical Formula 1, R1 to R3 are each independently a hydrogen atom, or a linear or branched alkyl group having 1 to 12 carbon atoms.

14. The 1,4-cis polybutadiene of claim 13, wherein the lanthanide rare earth element-containing compound includes a neodymium compound in which, in Chemical Formula 1, R1 is a linear or branched alkyl group having 6 to 12 carbon atoms, and R2 and R3 are each independently a hydrogen atom or a linear or branched alkyl group having 2 to 8 carbon atoms, but R2 and R3 are not both hydrogen atoms at the same time.

15. The 1,4-cis polybutadiene of claim 1, wherein the lanthanide rare earth element-containing compound includes any one or a mixture of two or more selected from the group consisting of Nd(2,2-diethyl decanoate)3, Nd(2,2-dipropyl decanoate)3, Nd(2,2-dibutyl decanoate)3, Nd(2,2-dihexyl decanoate)3, Nd(2,2-dioctyl decanoate)3, Nd(2-ethyl-2-propyl decanoate)3, Nd(2-ethyl-2-butyl decanoate)3, Nd(2-ethyl-2-hexyl decanoate)3, Nd(2-propyl-2-butyl decanoate)3, Nd(2-propyl-2-hexyl decanoate)3, Nd(2-propyl-2-isopropyl decanoate)3, Nd(2-butyl-2-hexyl decanoate)3, Nd(2-hexyl-2-octyl decanoate)3, Nd(2-t-butyl decanoate)3, Nd(2,2-diethyl octanoate)3, Nd(2,2-dipropyl octanoate)3, Nd(2,2-dibutyl octanoate)3, Nd(2,2-dihexyl octanoate)3, Nd(2-ethyl-2-propyl octanoate)3, Nd(2-ethyl-2-hexyl octanoate)3, Nd(2,2-diethyl nonanoate)3, Nd(2,2-dipropyl nonanoate)3, Nd(2,2-dibutyl nonanoate)3, Nd(2,2-dihexyl nonanoate)3, Nd(2-ethyl-2-propyl nonanoate)3 and Nd(2-ethyl-2-hexyl nonanoate)3.

16. The 1,4-cis polybutadiene of claim 5, wherein, in the modified methylaluminoxane, 50 mol % to 90 mol % of a methyl group of the methylaluminoxane is substituted with a hydrocarbon group having 2 to 20 carbon atoms.

17. The 1,4-cis polybutadiene of claim 5, wherein the aliphatic hydrocarbon-based solvent includes any one or a mixture of two or more selected from the group consisting of linear, branched or cyclic aliphatic hydrocarbon having 5 to 20 carbon atoms.

18. The 1,4-cis polybutadiene of claim 5, wherein the halogen compound includes any one or a mixture of two or more selected from the group consisting of elemental halogen compounds, interhalogen compounds, halogenated hydrogen, organic halides, non-metal halides, metal halides and organic metal halides.

19. The 1,4-cis polybutadiene of claim 5, wherein the catalyst composition does not include diisobutylaluminum hydride.

* * * * *